United States Patent [19]

Shaw

[11] Patent Number: 5,188,613
[45] Date of Patent: Feb. 23, 1993

[54] NONREUSABLE SYRINGE WITH SAFETY INDICATOR

[76] Inventor: Thomas J. Shaw, 1510 Hillcrest, Little Elm, Tex. 75068

[21] Appl. No.: 843,479

[22] Filed: Mar. 6, 1992

Related U.S. Application Data

[63] Continuation-in-part of Ser. No. 679,627, Apr. 3, 1991, Pat. No. 5,120,310.

[51] Int. Cl.⁵ ............................................. A61M 5/32
[52] U.S. Cl. ...................................... 604/195; 604/111
[58] Field of Search ............... 604/111, 110, 195, 187, 604/263, 198, 218, 220, 136, 137, 138

[56] References Cited

U.S. PATENT DOCUMENTS 5,084,029 1/1992 Tagliaferri et al. ................ 604/195
5,092,853 3/1992 Couvertier, II .................... 604/195

Primary Examiner—John D. Yasko
Attorney, Agent, or Firm—Hubbard, Thurman, Tucker & Harris

[57] ABSTRACT

A nonreusable syringe is provided having an automatically retracting hypodermic needle to prevent accidental injury after injection or undesirable reuse of the syringe. The needle is retracted by a spring located behind the syringe piston and disposed to prevent reextension of the needle after use. A locking mechanism holds the needle in position for injection. The piston includes means to release the locking mechanism as injection is completed to automatically retract the needle into the syringe. The syringe tip seal is not in frictional contact with the needle, eliminating drag on the needle during retraction. A safety indicator is provided to indicate previous use.

26 Claims, 5 Drawing Sheets

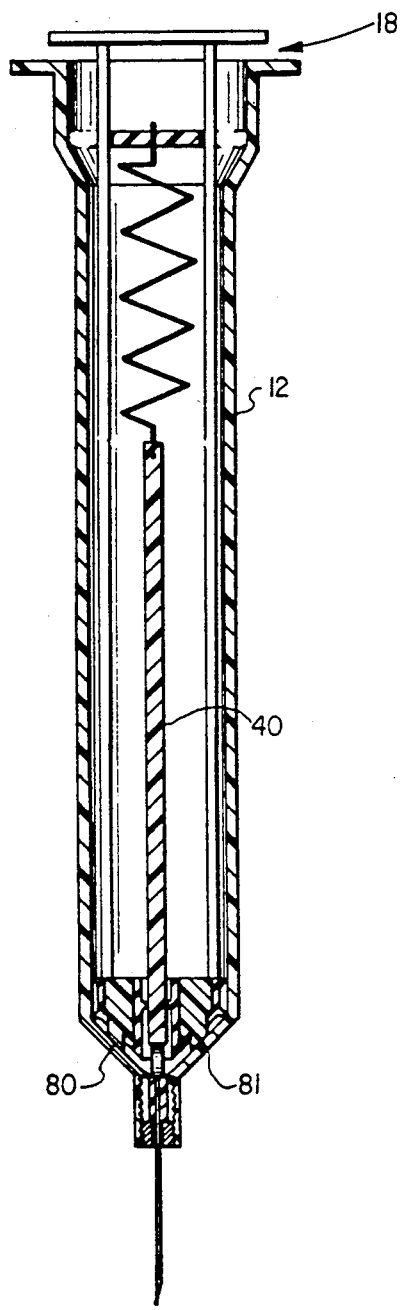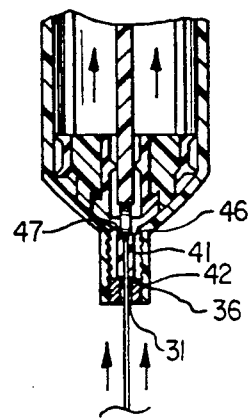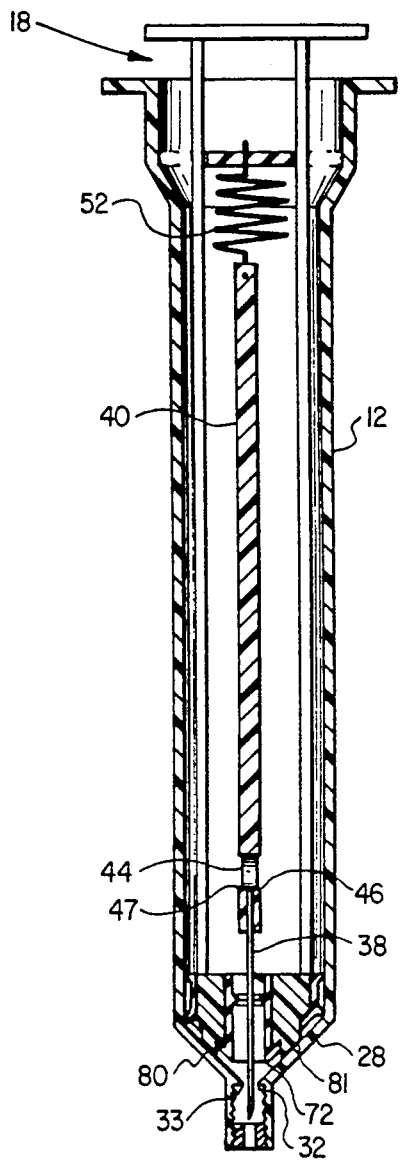
FIG. 4
FIG. 5
FIG. 6

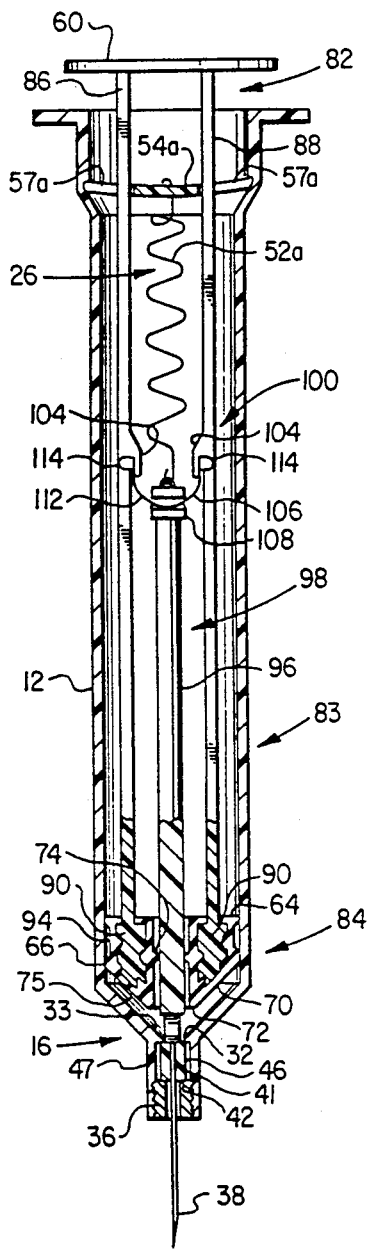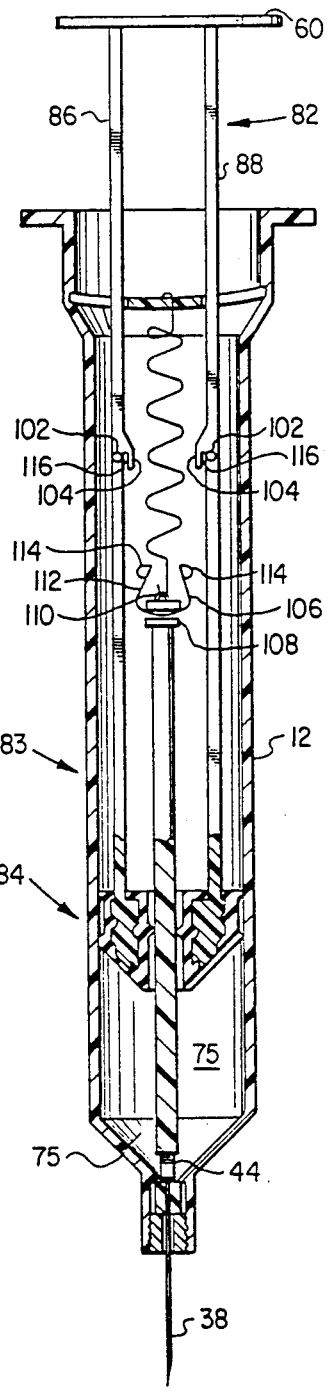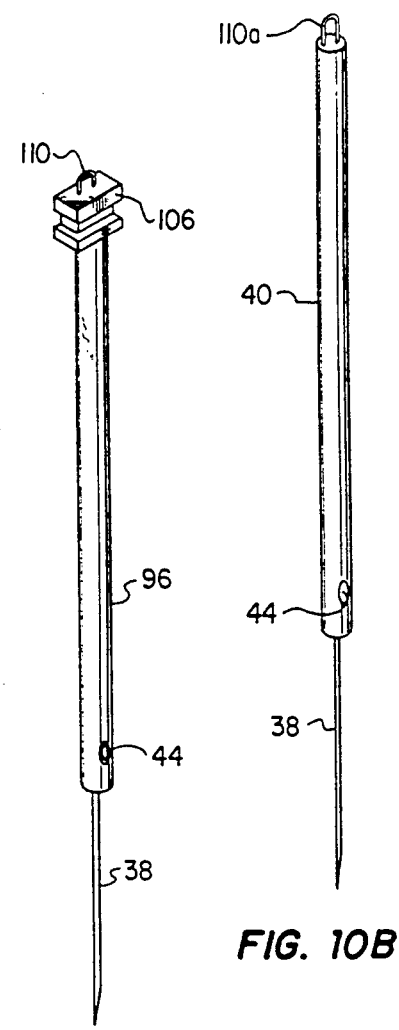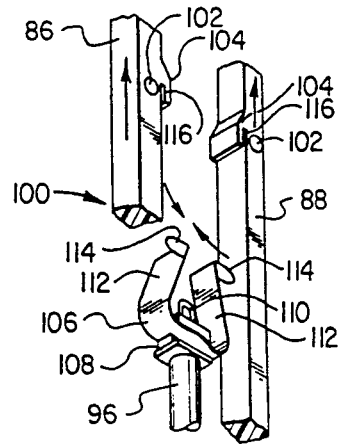
FIG. 7
FIG. 8
FIG. 10A
FIG. 10B
FIG. 9

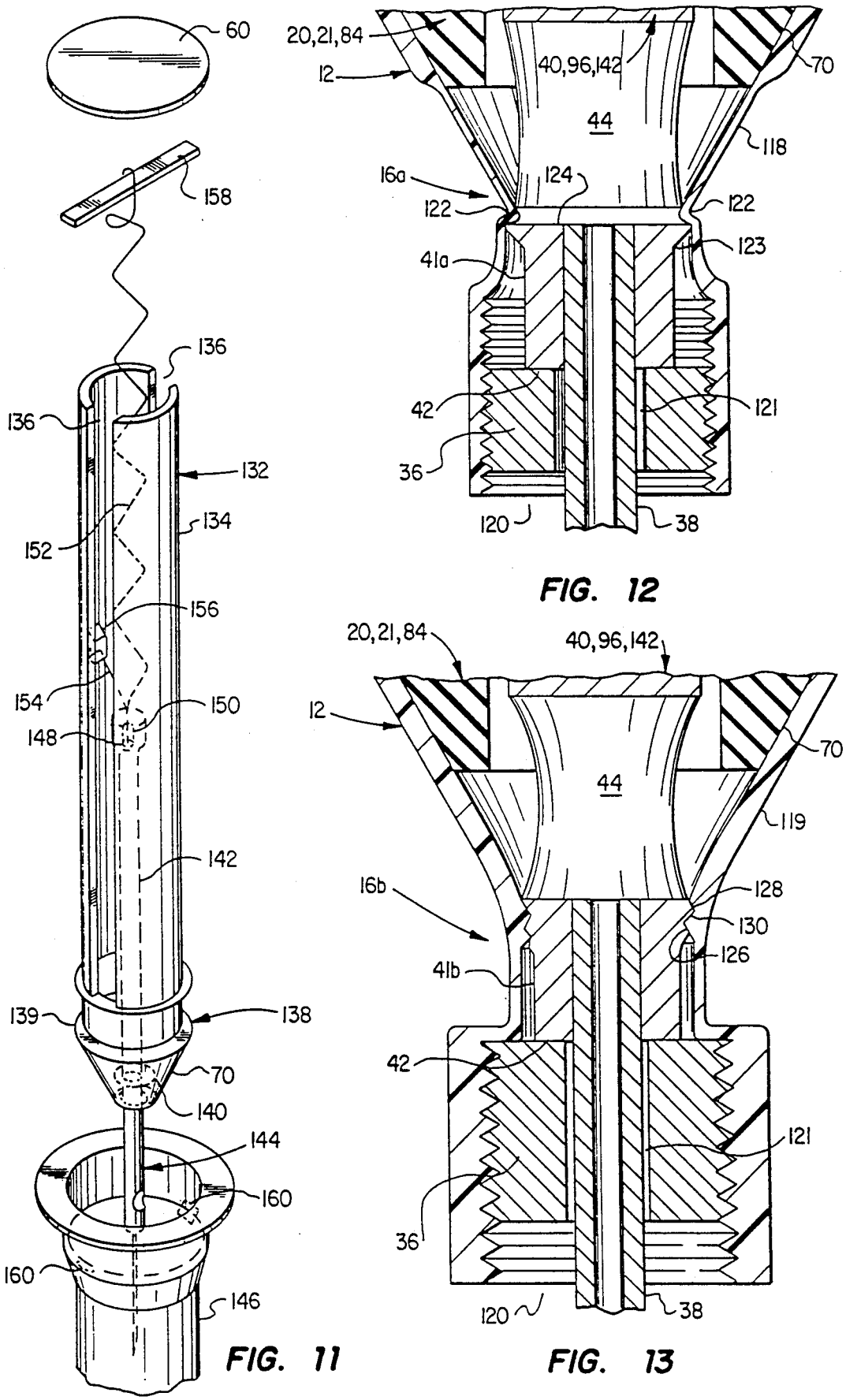

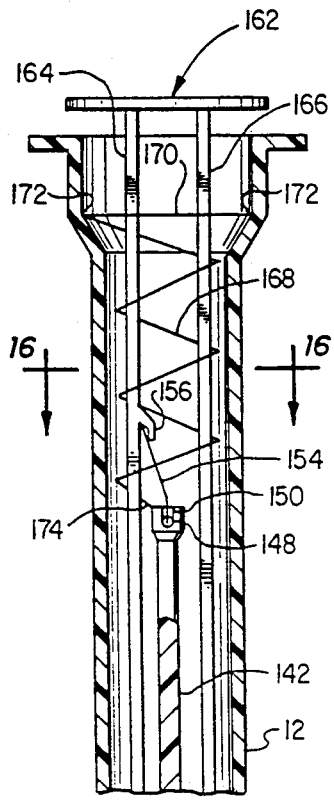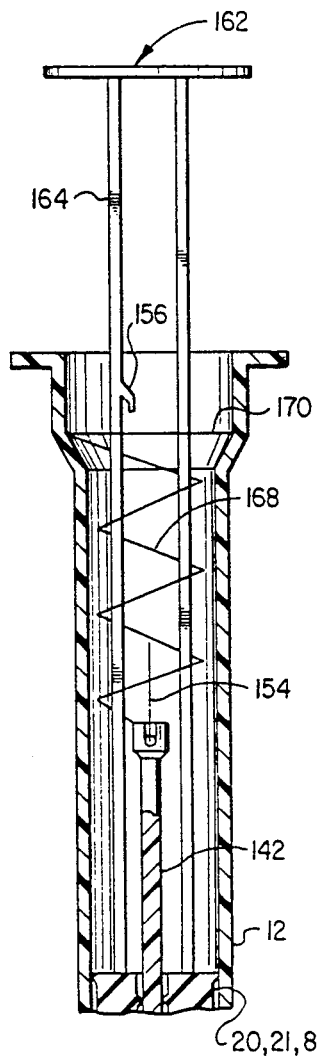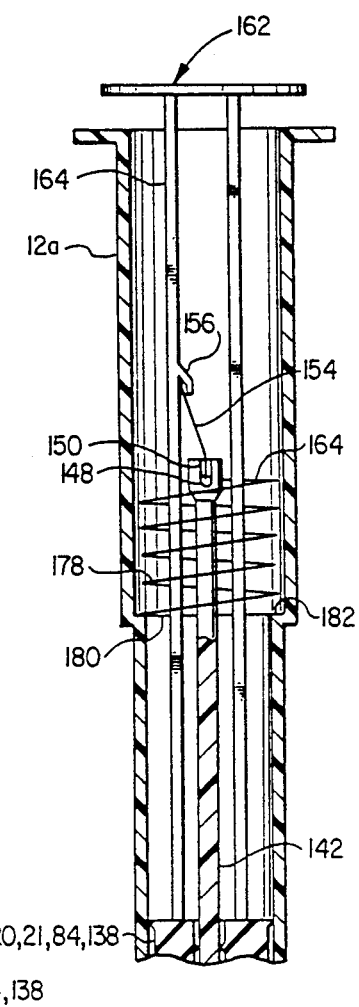
FIG. 14   FIG. 15   FIG. 17
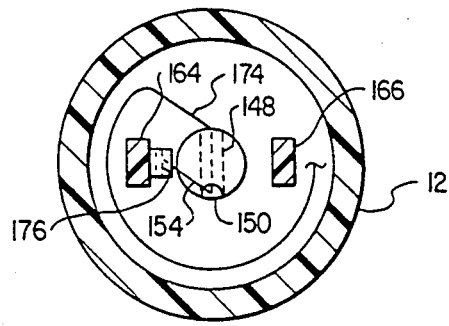
FIG. 16

NONREUSABLE SYRINGE WITH SAFETY INDICATOR

CROSS REFERENCE TO RELATED APPLICATION

This is a continuation-in-part of my U.S. patent application Ser. No. 07/679,627, entitled Nonreusable Syringe, filed Apr. 3, 1991 now U.S. Pat. No. 5,120,310.

BACKGROUND OF THE INVENTION

This invention relates to a syringe device and more particularly to a nonreusable syringe having an automatically retracting hypodermic needle to prevent reuse of the syringe.

Many communicable diseases are commonly spread by contacting bodily fluids of an infected person. Reuse of hypodermic syringes is one of the most common ways for such contact, particularly among drug users. Various mechanisms are provided in medical facilities for the disposal or destruction of syringes and hypodermic needles after usage. However, it is not uncommon for a medical worker to be scratched or punctured by a needle after usage and before disposal, resulting in injury and exposure to disease.

Various syringes have been devised for retracting the needle into the syringe or otherwise disarming the syringe after it has been used. U.S. Pat. No. 4,874,382 to Lindemann et al. discloses a safety syringe having a needle which is retracted into a protective sheath inside the syringe. After the needle has been used, it may be withdrawn into the sheath by a coil spring which is actuated by the user depressing a trigger mechanism. However, such a device provides no protection against a user desiring to reuse the syringe who would simply not activate the mechanical trigger.

Another device shown in U.S. Pat. No. 4,838,869 to Allard also provides a protective sheath within the syringe into which the hypodermic needle is withdrawn after usage. In this device, depression of the syringe plunger engages protrusions holding the spring loaded needle so as to release the needle for retraction into the sheath. However, the use of a protective sheath substantially reduces the volume available in the syringe for fluid. Moreover, the strength of the spring is substantially limited by restricting its size to the diameter of the sheath, limiting the effectiveness of overcoming friction of the seal against the needle so as to retract the needle. Furthermore, the use of an inner sheath in a syringe restricts the view of the user in detecting undesirable bubbles in the syringe fluid.

An effective means of indicating that the syringe plunger has been moved is a needed safety feature to assure that a new syringe has never been used.

SUMMARY OF THE INVENTION

The present invention provides a nonreusable syringe apparatus which overcomes these problems in the prior art. The syringe has a retractable hypodermic needle mounted on a thin rod which extends to a large spring located behind the plunger. Thus, strong retraction force is applied without using syringe fluid space. Also, the hypodermic needle is not in substantial contact with the syringe seal so that there is essentially no friction force to be overcome in retracting the needle. In addition, the needle retracts automatically as soon as the syringe has released all of its fluid, eliminating any chance of accidental injury or intentional reuse of the needle once the fluid has been emitted. Moreover, as retraction begins, the needle breaks the vacuum with the skin so that undesired blood and body fluids are not extracted from the patient as the needle is removed.

In one embodiment, the present invention comprises a spring having a retractable needle for injecting fluid into a body which includes a hollow tubular member providing the cavity for the fluid, a plunger disposed partially within the tubular member having piston means in slidable seal contact with the inner walls of the tubular member to form a chamber for the fluid, needle means in the fluid chamber in sealed contact with one end of the tubular member and having a needle extending therethrough to inject the fluid, resilient means disposed entirely behind the piston means and connected to the needle means, being biased to retract the needle into the fluid chamber, lock means connecting the needle means to the tubular member to maintain the seal contact of the needle means to the tubular member, and release means to automatically disengage the lock means and enable retraction of the needle upon actuation of the plunger.

In one variation of this embodiment, the plunger comprises an oppositely spaced apart pair of plunger arms in which the resilient means is positioned around the outside of the arms to allow for a larger and stronger resilient means, if desired.

In a third embodiment, the resilient means is connected to the top of a thin rod means which moves with the needle. The rod means has a biased safety clip which releasably engages the plunger in its depressed position with respect to the tubular body of the syringe. The biased slip covers brightly colored indicia. When the plunger is partially retracted, the clip releases from the plunger and the colored indicia becomes visible through the wall of the syringe to indicate that the plunger has been moved from its shipping position. This serves as a permanent warning that the syringe has been made ready to use, as a further check on possible tampering. Once the clip has been released, it cannot be reengaged and does not interfere with the automatic retraction of the needle assembly which occurs as before when the plunger is fully depressed.

In a fourth embodiment, the plunger assembly may comprise a substantially cylindrical shape forming a hollow cylinder having slots for a spring retaining means fixed to the syringe body to allow the plunger to be moved within the body without interference. The needle assembly may have an arming bar to facilitate seating the needle assembly in the locking means. The arming bar automatically arms the needle assembly for retraction when the plunger is moved.

A fifth embodiment employs a resilient member surrounding the plunger, having one end supported by a stop in the tubular body and an opposite end connected to the upper end portion of a needle rod tensioned to exert a retraction force. A biased arming bar at the end of the needle rod engages a retainer on the plunger when the plunger is depressed. Force exerted on the plunger is transmitted to the needle assembly by the arming bar sufficient to engage a locking means which holds the needle assembly. When the plunger is withdrawn, the arming bar is triggered to spring into a non-interfering neutral position which arms the needle assembly automatically for subsequent retraction by the resilient member. The arming bar serves to simplify assembly, protects against accidental "firing" and itself visibly shows that the plunger has not been moved previously.

A sixth embodiment has the same features as the fifth embodiment except that the stop is positioned down inside the tubular body and the upper end of the needle rod member extends above the spring, one end thereof being connected to the needle assembly to provide retraction force by compression of the spring. A large spring can be used to provide a greater retraction force. Assembly is simplified.

BRIEF DESCRIPTION OF THE DRAWINGS

FIG. 4 is an elevational cross-section view of the syringe in FIG. 3 with the plunger fully depressed;

FIG. 5 is an exploded detailed view in cross-section of the lower portion of the syringe shown in FIG. 4; and FIG. 6 is an elevational cross-section view of the syringe shown in FIG. 3 in unarmed state with the needle retracted into the syringe cylinder.

FIG. 7 is an elevational cross-section view of the third embodiment. A biased clip mechanism engages the plunger in its depressed position with indicia covered by portions of the clip;

FIG. 8 shows the embodiment of FIG. 7 with the plunger partially retracted to release the clip to its unbiased position, revealing warning indicia on the plunger;

FIG. 9 is a detail perspective view of the clip and portions of the plunger rods and indicia just after the clip has been separated and released from the plunger;

FIG. 10A is a perspective view of a portion of the needle assembly with a clip retainer mounted on the rod which holds the needle;

FIG. 10B is a perspective view of the needle and rod with a fastening loop on one end;

FIG. 11 shows an exploded perspective view of a fourth embodiment having a plunger assembly formed as a hollow cylinder having slots accepting of a spring retaining bar and equipped with a spring loaded arming bar;

FIG. 12 shows a partial elevational cross-section of any of the embodiments showing a modified form of a release means holding a needle assembly in armed state;

FIG. 13 shows a partial elevational cross-section of any of the embodiments showing another modified form of a release means and needle assembly in armed state;

FIG. 14 is a partial elevational cross-section of a fifth embodiment showing an alternate arrangement of the plunger and resilient means and a spring loaded arm which serves as an arming bar shown in unarmed state;

FIG. 15 is a partial elevational cross-section of the syringe of FIG. 14 showing the armed state which permanently results when the plunger is partially withdrawn from the hollow body to disengage the spring loaded arm;

FIG. 16 shows a cross section on line 16—16 of FIG. 14 with an end of the spring loaded arm in a retainer on the plunger; and FIG. 17 is a partial elevational cross-sectional view of a sixth embodiment showing another alternate arrangement of the plunger and resilient means including a spring loaded arming bar in initial unarmed position.

DETAILED DESCRIPTION OF PREFERRED EMBODIMENTS

Figure 1:
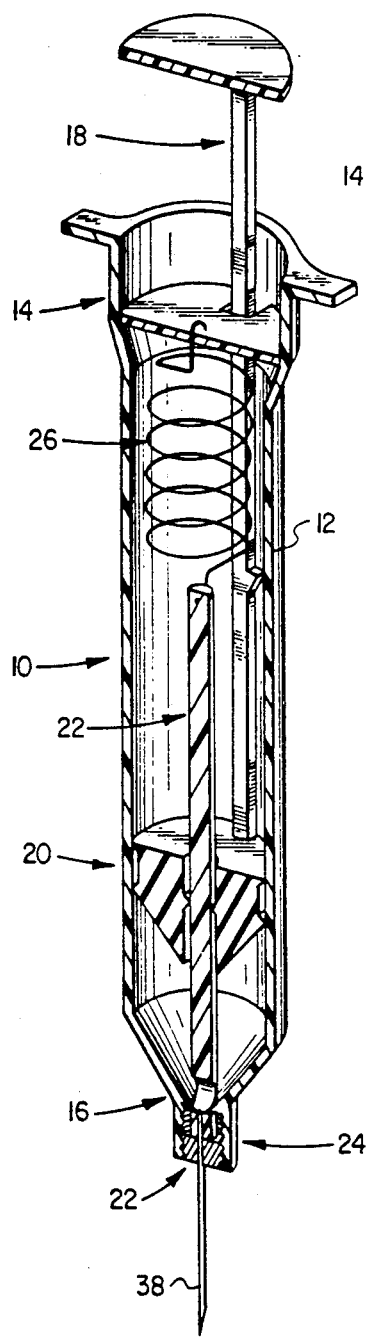
FIG. 1 is a perspective cross-section view of a syringe comprising a preferred embodiment of the present invention.

In the description that follows, like parts will have the same reference numerals insofar as possible. Subscripts will be used to indicate slightly modified versions of similar parts that have reference numerals without subscripts.

With reference to FIG. 1, a hypodermic syringe 10 is shown comprising a cylindrical tube 12 having an open end 14 and a closed end 16. A plunger assembly 18 extends out of the open end of the syringe tube and is connected to a piston assembly 20 which is slidably movable along the inner walls of tube 12. A needle assembly 22 includes a needle 38 extending through closed end 16 of tube 12. A lock assembly 24 holds the needle assembly in position with needle 38 extended. Needle assembly 22 is connected to a resilient spring assembly 26 which is biased to retract needle assembly 22 into tube 12.

Syringe 10 is constructed to retract needle 22 into tube 12 automatically during the course of use of the syringe as the last step of injecting fluid into a patient. The needle retraction prevents any possibility of infection of a health care worker by accidental contact with the needle after injection. The automatic needle retraction also prevents any further use of the needle for further injections.

Figure 2:
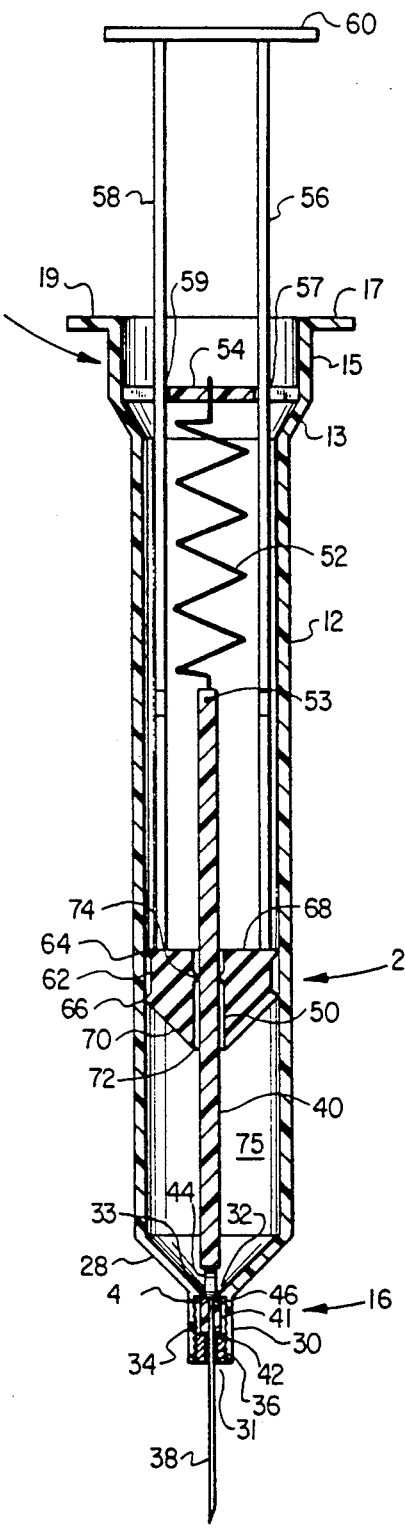
FIG. 2 is an elevational cross-section view of the syringe of FIG. 1 showing the syringe in armed condition with the needle extended.

Looking now at FIG. 2, tube 12 is preferably a cylinder having a unitary radius throughout except at open end 14 and closed end 16. The radius of tube 12 increases near open end 14 to form an annular ridge 13. Tube 12 extends further at the increased radius to form wall 15 terminating in radially extending fingers 17 and 19.

Closed end 16 of tube 12 is formed by a cone-shaped section 28 in which the radius of tube 12 tapers to form a restricted tube 30 having a small axially centered tubular opening 31. At the point where cone-shaped section 28 joins restricted tube 30, lock tabs 32 and 33 extend radially inward to form a locking mechanism to be discussed later. The interior wall of restricted tube 30 has threads 34 and a threaded tubular tip seal 36 positioned to seal off tubular opening 31.

A hollow sharpened needle 38 extends through restricted tube 30 and tip seal 36. The other end of needle 38 is inset into a rod 40 which extends downward through piston assembly 20 and into tubular opening 31 of tube casing 12. As best seen in FIG. 5, rod 40 has a rod end 41 forming a shoulder 42 which abuts at the end of tip seal 36 thereby sealing off tubular opening 31. Thus needle 38 is not in contact with seal 36, eliminating any frictional pull on needle 38 as it retracts. Needle 38 is inset in rod end 41 and extends to a transverse hole 44 in rod 40 which communicates with the hole in hollow needle 38. At the junction of transverse hole 44 and rod end 41, shoulders 46 and 47 abut against lock tabs 32 and 33, which holds needle 38 in its extended position as shown.

Rod 40 extends axially through a channel 50 in piston 20. A spring 52 is connected through a hole 53 in the end of rod 40 and extends axially to connect to a spring support member 54 resting radially on the slanted annular ridge 13 of tube 12. Preferably, support member 54 is permanently affixed to the walls of tube 12 to prevent removal of needle assembly 22 after use.

Plunger assembly 18 consists of two plunger arms 56 and 58 extending through apertures 57 and 59 in spring support 54 and terminating at piston assembly 20. Plunger bars are connected at their upper end to a flat disk 60 for depressing the plunger during use. Upon depression of plunger 18, annular tip 72 impacts lock tabs 32 and 33 directly and flexes them away from shoulders 46 and 47 of rod end 41, thereby enabling retraction of needle 38.

Piston assembly 20 is comprised of a circular piston 62 slidable along the inner walls of tube 12 and having upper and lower annular seals 64 and 66 in slidable contact with the inner walls of tube 12 and forming a fluid seal therewith. Piston 62 has a flat upper surface 68 to which plunger arms 56 and 58 are attached. A conical lower surface 70 slants inward from annular seal 66, ending in an annular tip 72 which forms the lower end of tubular channel 50. Piston 62 also has an annularly extending seal 74 extending within tubular channel 50 to form a fluid seal with rod 40. Thus, a fluid chamber 75 is formed by conical surface 70, annular seal 74, and outer seals 64 and 66 at the upper end. The rest of the fluid chamber 75 is formed by the walls of tube 12 which taper downward in cone-shaped section 28 to restricted tube 30 which is sealed off by tip seal 36 and rod end 41.

Figure 3:
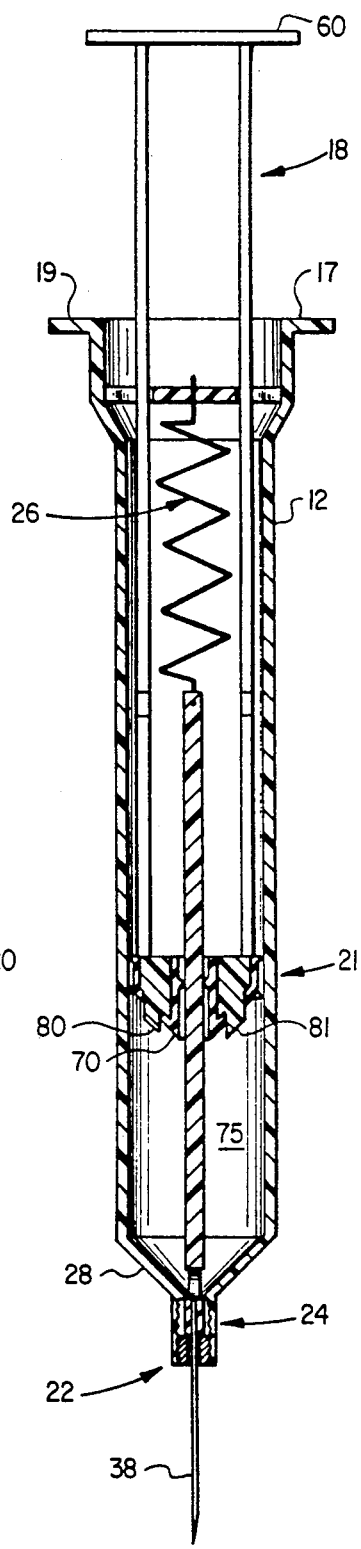
FIG. 3 is an elevational cross-section view of another embodiment of the present invention showing the syringe in armed state with the needle extended.

An alternate embodiment is shown in FIG. 3 having the same structure as the syringe of FIGS. 1 and 2 except with regard to piston assembly 21. In this embodiment, piston assembly 21 is identical to piston assembly 20, except that it includes dual cusp abutments 80 and 81 protruding downward from conical surface 70 to make contact with cone-shaped section 28 of the syringe tube 12 when the plunger assembly 18 is fully depressed.

Spring support 54 preferably also includes a shipping safety stop (not shown) comprising a rectangular-shaped member resting on top of spring support member 54 so as to impact the lower surface of plunger disk 60. The shipping safety stop is of sufficient height to prevent the plunger assembly 18 from being depressed to the point where piston assembly 20 impacts locking assembly 24 releasing needle assembly 22 to be withdrawn into the tube. The safety stop may also include a spring biased to automatically fold the stop onto spring support 54 once the plunger assembly 18 has been retracted so as to allow a full stroke of the plunger 18 during injection.

Regarding materials, preferably the spring 52 is steel, needle 38 is corrosive-resistant steel, plunger 62 is a medium-soft rubber, tip seal 36 is medium-hard rubber and all other materials are plastic.

The operation of syringe 10 will now be described. As shown in FIG. 3, the plunger assembly 18 is retracted to draw fluid into chamber 75 through hollow needle 38. After fluid is drawn into chamber 75, it may be injected by inserting needle 38 into the body of a patient and by grasping fingers 17 and 19 while pressing on plunger disk 60, thus moving the plunger assembly 18 into the syringe casing 12. During depression of the plunger assembly 18, fluid is forced out of chamber 75 through needle 38 into the patient.

With reference now to FIGS. 4, 5 and 6, when plunger assembly 18 is fully depressed, the dual cusp abutments 80 and 81 impact the cone-shaped section 28 of tube 12. Preferably section 28 is thin-walled and designed to flex ovally when pushed by dual cusp abutments 80 and 81 so as to flex the lock tabs 32 and 33 holding the needle assembly 24 in place. Lock tabs 32 and 33 then release shoulders 46 and 47 of rod end 41, as best seen in FIG. 5. The resulting action enables spring 52 to fully retract rod 40, thereby retracting needle 38 completely within syringe tube 12, as shown in FIG. 6.

In FIGS. 7 and 8, a third embodiment of the invention is illustrated. A hypodermic syringe 83 has a hollow tubular body 12, a plunger assembly 82 with safety indicator, piston assembly 84 and needle assembly 98. Safety indicator plunger assembly 82 is connected to piston assembly 84, which is quite similar to piston assemblies 20 and 21. Plunger assembly 82 has plunger arms 86,88 which are connected by a disk 60. The lower extremity of arms 86,88 has an annular portion 90 which serves as a support for rubber piston 94 which has the same attributes as piston 62 of piston assembly 20. Consequently, the same reference numerals will be used to denote like portions of piston assembly 84. It has a conical lower surface 70, annular tip 72, annular seals 64 and 66, and an internal annular seal 74 to seal elongated rod member 96 of needle assembly 98. The lower end of the rod member 96 is connected to needle 38 and in all respects is the same as shown in FIG. 2. A resilient spring assembly 26 includes a resilient spring member 52. Spring 52 is connected to a spring support member 54a to indicate that it is slightly modified from support member 54 to take into account the slightly closer spacing of arms 86,88 which necessitates deeper apertures 57a in which the plunger arms ride.

FIGS. 7 and 8 show the operation of a safety assembly 100 comprising brightly covered warning indicia 102 and retainers 104 on plunger arms 86,88 (FIG. 9) and a biasable member 106 mounted on holder 108 fixed to the upper end of the elongated rod member 96. FIG. 10A best shows the holder 108 having connector 110 for attaching resilient member 52a. FIG. 10B shows a connector 110a on a rod 40 as an anchor for a resilient spring.

Returning to FIG. 9, biasable member 106, holder 108 and connector 110 are an extension of the needle assembly 98. Biasable member 106 may be a spring clip having a pair of cooperating arms 112 or eared extensions, having ears 114.

In operation arms 112 are biased to releasably engage cooperating slots 116 of retainers 104 in FIGS. 7 and 8. Ears 114 are adapted to cover indicia 102. When plunger 82 is pushed down, biasable spring member 106 is strong enough to transfer the downward force to needle assembly 98 and seat it in locked operative position with tip 41 in contact with seal 36 and the lock means of the tubular body 12 engaged with the lower end portion of rod member 96. This is the way the syringe is furnished for use.

When plunger 82 is withdrawn in FIG. 8 to fill chamber 75 with injection fluid, member 106 being connected to locked rod 96 resists movement and cooperating arms 112 are pulled from retainers 104 and slots 116. This allows biased arms 112 of member 106 to irreversibly close toward the center which arms the needle assembly for subsequent retraction when it is released from the lock means. The warning indicia are visible through the clear wall of the syringe to indicate that the syringe has been used.

When the plunger is depressed to inject the fluid, there is clearance between the now unbiased member 106 and retainers 104. Plunger 82 can move down until piston assembly 84 releases the lock means and the needle assembly is free to move upward into tubular body 12 under influence of resilient spring 52a. The needle is completely retracted into the body and cannot be reused. The warning indicia remain uncovered.

In FIGS. 12 and 13, hollow tubular body 12 may have a modified closed end 16a or 16b. Body 12 has a lower end 16a,16b having a tapered conical shaped wall 118,119. The tip 41 of the elongated rod may be slightly modified to tip 41a, 41b as shown.

In FIG. 12 the lower end 16a has a tubular axially-centered opening 120 threaded to hold tip seal 36 therein. Annular locking means 122 located above opening 120 comprises an annular ring formed in wall 118 for engaging an annular locking surface 124 on the rod tip or lower end 41a which terminates in sealing surface 42. Locking surface 124 is spaced above sealing surface 42 to simultaneously lock the tip and seal against seal 36. Annular locking means 122 is formed around the most restrictive portion of tapered wall 118 of body 12. Lower end 41a of rod member 40,96,142 is preferably relieved starting at 123 to reduce frictional resistance during retraction. Gap 121 separates seal 36 from needle 38 to eliminate friction there. When the plunger of choice is depressed, wall 70 of pistons 20,84,138 or annular protrusions on piston 21 flex or spread wall 118 to unlock and release the seated needle assembly which is then retracted. Wall 70 may have a slightly different taper from wall 118 to facilitate release. It is desirable to minimize empty space above seal 36 around tip 41a below the lock means to reduce air entrainment.

In FIG. 13, modified lower end 16b has tubular axially centered opening 120 threaded to receive seal 36. At the most restricted portion of conical tapered wall 119 are several internal threads 126 comprising annular locking means 128. Cooperating threads 130 are formed on modified rod end 41b which like modified end 41a may be used with any of the elongated needle rods disclosed herein. Cooperating threads 130 comprise a locking surface on the lower end of an elongated rod member 40,96,142. The needle rod member may be screwed into position with surface 42 against seal 36. Downward force on the needle rod may also engage locking means 128 by flexing of wall 119 to slip the threads 126,130 relative to each other and seat needle rod tip member shoulder 42 in sealed contact with seal 36 with needle 38 held extended in operative position.

Downward force on the piston when the plunger is depressed causes surface 70 (or a protrusion thereon) to come into contact with and slightly flex and expand wall 119 to release the cooperating threads 126,130 of locking means 128 so that the needle rod is free to respond to retraction force supplied by a resilient means as has been described.

FIG. 11 represents a fourth embodiment having a plunger assembly 132 formed as a hollow cylinder 134 having opposed longitudinal slots 136. Piston assembly 138 is located at the lower end of plunger 132. The piston may be molded integral with or fixed to plunger 132 or plunger 132 may have a piston 20 or 21. Piston assembly 138 has a conical surface 70 for releasing a locking means. Piston assembly includes a groove 139 for an "O" ring type seal against the inner walls of syringe body 146. Piston 138 also has a sliding seal 140 to seal rod 142 of needle assembly 144. This seal may be an "O" ring seal. Plunger assembly 132 fits into syringe body 146 which may have a locking and release mechanism for the needle assembly like FIGS. 1-6, 7, 12 or 13.

The upper end of elongated rod 142 has transverse opening 148 intersecting upright groove 150 extending to the distal upper end of the rod. Opening 148 and groove 150 secure one end of spring 152. Connected to the upper end portion of rod 142 is an arming bar 154 which is releasably engaged with retainer 156 on the wall of cylinder 134. Operation of the arming bar will be discussed further in connection with FIGS. 14-16. The opposite end of spring 152 is supported by bar 158 which is fixed in notches 160 at the top of tubular body 146 and serves as a guide to orient the plunger, if desired, while it is moved. The slotted openings 136 permit the plunger to be withdrawn without interference from bar 158. Thumb disc 160 is secured to the upper end of the plunger. Release of the arming bar occurs as soon as the plunger is moved upward from its fully depressed position with the needle assembly locked. It operates like FIGS. 14-17.

FIGS. 14-16 illustrate the idea of the arming bar in a fifth embodiment, it being understood that the bottom half of the syringe is like any of the FIGS. previously discussed. Rod 142 extends upwardly in sliding sealed contact through a piston assembly 20, 21, 84 or 138, which in this case would be connected to and operated by slightly modified plunger assembly 162 having a pair of arms 164,166. Rod 142 extends downwardly below the piston as part of a needle assembly which is releasably locked and unlocked by the piston as has been previously described in connection with the other FIGS. FIG. 14 shows the position with the plunger and piston fully depressed and the needle assembly locked as in FIG. 7.

Spring 168 is a resilient member which circumscribes and surrounds plunger arms 164,166, having an enlarged upper end 170 secured in an annular stop 172 formed at a flared open end of hollow tubular body 12 and preferably sealed in place by adhesive or mechanical means so that the piston cannot be removed.

The opposite lower end 174 of spring 168 is connected to the upper end portion of elongated rod member 142 via transverse opening 148 and interconnected upright groove 150. Spring loaded arming bar 154, which conveniently comprises an extension of spring wire 158, extends upwardly through groove 150 to releasably engage a retainer 156 formed on plunger arm 164. Spring 168 is biased to exert retraction force on elongated rod 142. During assembly the arming bar maintains the positional relationship between the plunger assembly and rod member as shown in FIG. 14. Arming bar 154 may include bent end portion 176, best seen in FIG. 16, to engage a slot in retainer 156.

Arming bar 154 is sturdy enough to engage the locking means and locking surface on tubular body 12, and a rod member 40,96,142, when downward force is applied to the rod member via the arming bar when the plunger is depressed. This is the preferred position of the syringe for shipment before use.

FIG. 15 illustrates what happens when the needle assembly 162 is armed by moving plunger 162 upward from the pre-use position in order to draw fluid into the syringe for injection. Rod 142 remains locked with the needle assembly in operational position with needle 38 extended. Retainer member 156 moves upward and arming member 154 is released and triggered to its neutral unbiased position axially centered in body 12. Spring member 168 is now poised to retract the needle assembly immediately when the needle assembly is subsequently unlocked in response to full downward movement of the plunger. The arming member is permanently and irreversibly out of the way once it is armed in this manner.

It should be noted that the arming bar makes assembly simple by seating the needle assembly to locked position when the plunger is depressed. It prevents accidental retraction of the needle if someone should apply force to the plunger before the plunger is withdrawn for filling. It serves as a visible signal that the syringe has never been used.

FIG. 17 represents a sixth embodiment of the resilient spring, plunger and body arrangement that allows for a resilient spring which provides retraction force to a needle assembly by compression in the spring member. Spring 178 has a lower end 180 resting on annular ledge 182 formed in modified hollow tubular body 12a. Upper end 184 of spring 178 is connected via transverse opening 148 and upright groove 150 in the upper end of elongated rod member 142 as previously described. The distal upper end portion of spring 178 may conveniently extend upward to serve as spring loaded arming bar 154 which is biased to releasably engage retainer 156 on plunger arm 164 of plunger assembly 162. The operation is as described with respect to FIGS. 14–16. In this case, stop 182 is positioned below the upper end of the elongated rod member so that the spring can operate by compression to retract the needle assembly.

The advantages and improvements of the present invention are now clearly seen. By placing the spring 52 completely behind the piston assembly 20, a larger spring can be used without displacing the volume of fluid chamber 75. Only a small thin rod 40 protrudes into the fluid chamber. Moreover, since the needle 38 is not in contact with seal 36, essentially no friction is present to oppose action of the spring.

A safety indicator shows visibly whether the syringe has ever been used. Indicia are permanently uncovered or an arming bar permanently released if the syringe has ever been used.

An additional advantage with the present invention is that essentially all of the injection fluid is removed from fluid chamber 75 before the needle retraction mechanism is activated. Thus no fluid is lost through the tubular opening 31 after the seal is broken and the needle 38 is retracted. At the same time, the mechanism of the present invention prevents a user from cleaning and reusing the assembly, because the only way to clean the mechanism is to remove all of the fluid in the syringe, which would activate the retraction device. Once the needle has been retracted into the cylinder of the syringe, it cannot be accessed unless the cylinder itself is broken open. Thus, as long as there is no residue within the fluid chamber, one can be assured that the syringe has not been used.

An important advantage of the present invention is that the needle assembly is retracted automatically after all of the fluid has been forced out of the chamber. This automatic action prevents a medical worker or a patient from being inadvertently stuck by the needle after it has been withdrawn from the patient. It also prevents any further undesirable use of the hypodermic syringe by another user. Moreover, as the needle begins to retract at the point when the fluid injection has been completed, the fluid seal is broken and releases a vacuum formed between fluid chamber 75 and the patient, so that no bodily fluid is removed from the patient's body.

Some additional embodiments are included within the scope of this invention. The needle 38 and rod 40 may be combined as a single component. Also lock tabs 32 and 33 may be replaced by an annular lock ring, and dual cusps 80 and 81 may be replaced by an annular abutment. Other obvious variations may be made to the preferred embodiments shown without departing from the spirit of the invention or the scope of the claims.

What is claimed is:

1. A syringe having a retractable needle for injecting fluid into a body comprising:
   (a) a hollow tubular body member providing a cavity for the fluid, having an open end for insertion of a plunger;
   (b) a plunger disposed partially within the tubular member having piston means in slidable sealed contact with the inner walls of the tubular member to define a chamber for the fluid at one end of the tubular member;
   (c) a needle assembly within said tubular member having a needle in sealed contact with one end of the tubular member and extending therethrough to inject the fluid, the needle assembly including a rod having one end extending in sealed contact through said piston means and another end connected to said needle;
   (d) resilient means disposed behind the piston means and connected to said one end of the rod, biased to retract the needle into the tubular member;
   (e) lock means to lock the needle assembly in place with the needle extended from the tubular member;
   (f) warning indicia on the plunger covered by an extension of the needle assembly when the plunger is inserted, the warning indicia being permanently uncovered when the plunger is withdrawn to fill the chamber with fluid to be injected; and
   (g) release means to unlock the needle assembly and allow the resilient means to retract the needle after the plunger is fully depressed to inject the fluid in the chamber through the needle.

2. The syringe of claim 1 wherein the extension of the needle assembly is a biased member which engages one or more retainers on the plunger and is disengaged upon withdrawal of the plunger with the needle assembly locked in place.

3. The syringe of claim 2 wherein the biased member includes ears adapted to cover the warning indicia on the plunger when the biased member is engaged with said retainers and uncover the warning indicia when the biased member is disengaged.

4. The syringe of claim 3 wherein the biased member is a spring clip mounted on the rod, having eared extensions which cover the warning indicia and simultaneously engage cooperating slots on the plunger which comprise said retainers.

5. The syringe of claim 4 wherein the plunger comprises paired bars spaced apart on opposite sides of the rod and having a cooperating slot retainer on each bar and said spring clip has a pair of cooperating arms each engageable with one of said slot retainers.

6. The syringe of claim 2 wherein the plunger has a hollow cylindrical shape to fit within said tubular body and surround said rod and biased member.

7. The syringe of claim 6 wherein the said one or more retainers have arcuate portions which follow the inside surface of the hollow plunger member to provide extended crevices for frictional engagement of said biased member.

8. A medical device having a retractable needle for injecting fluid into a body comprising:

(a) a hollow tubular body having an upper open end and a lower end with tapered walls and a tubular axially-centered opening at the lower end having a seal therein;

(b) a piston disposed within said tubular body in slidable fluid-sealed contact with the inner walls of the body, defining a fluid chamber below the piston;

(c) a plunger attached to said piston for sliding the piston within the body, the plunger extending out the upper open end of the tubular body;

(d) a needle assembly within said tubular body, having a needle in operative position extending through the opening in the lower end of the tubular body past the seal, and an elongated rod member having a lower end supporting the needle in fluid communication with said fluid chamber, the rod member extending upward through the piston in slidable sealed contact therewith and having an upper end portion extending substantially above the lower end of the tubular body;

(e) a resilient member connected between the elongated rod member of the needle assembly and the tubular body and biased to exert a retraction force on the needle assembly with the needle extending in operative position from said opening in the lower end of said tubular body, (f) annular locking means located adjacent the tubular axially-centered opening of the tubular body for engaging a locking surface on the lower end of the elongated rod member, to hold the needle assembly in operative position with the needle extended;

(g) a locking surface on the lower end of the rod member which cooperates with said annular locking means to engage and hold the needle assembly until released; and (h) said annular locking means and locking surface being released in response to force imposed by a release surface on the piston which comes into contact with the tapered walls at the lower end of the tubular body when the plunger is depressed to inject substantially all fluid from the chamber, whereupon the retraction force provided by the resilient member on the needle assembly immediately retracts the needle entirely within said body to prevent reuse of the device.

9. The device of claim 8 wherein said annular locking means is formed around the most restrictive portion of the tapered walls of the tubular body.

10. The device of claim 9 wherein the lower end of the rod member terminates in a sealing surface for sealing contact with the seal in the tubular axially-centered opening of the tubular body, said locking surface being spaced above the sealing surface, to simultaneously seal and lock.

11. The device of claim 10 wherein said lower end of the rod member is relieved between the sealing surface and the locking surface to reduce frictional resistance during retraction.

12. The device of claim 11 wherein said locking means and locking surface comprise cooperating threads by which the sealing surface of the rod member may be held against the seal in said tubular opening of the body.

13. The device of claim 12 wherein the release surface on the piston comprises a protrusion on the piston to contact the locking means and thereby release the needle assembly.

14. The device of claim 12 wherein the release surface on the piston comprises a protrusion extending from the piston to contact the tapered walls of the lower end of the tubular body causing the walls to flex and thereby release the locking means.

15. The medical device of claim 8 wherein the plunger has a hollow cylindrical wall adapted to fit within said tubular body, spaced around said elongated rod member.

16. The device of claim 15 wherein a bar member is supported across the open upper end of the tubular body to serve as a support for one end of the resilient member, the plunger having elongated slotted openings for the bar member which permit retraction of the plunger within the tubular body for filling without interference from the bar member.

17. The device of claim 16 wherein the bar member is fixed to the tubular body and serves as a guide to orient the plunger while it is being moved.

18. The device of claim 8 wherein said resilient member surrounds said plunger, having one end supported by a stop in the tubular body and an opposite end connected to the upper end portion of the elongated rod member to exert said retraction force when the needle assembly is locked in operative position.

19. The device of claim 18 wherein said resilient member is a spring member biased to exert said retraction force.

20. The device of claim 19 wherein the opposite end of the spring member connected to the upper end portion of the elongated rod member includes an arming bar engageable with a retainer member on the plunger, operable to engage the needle assembly locking surface and locking means when downward force is applied on the plunger, said arming bar being triggered by upward movement of the plunger to arm the spring member for retraction of the needle assembly.

21. The device of claim 19 wherein said stop is positioned at the open upper end of the hollow tubular body to cooperate with an enlarged end portion of the spring member to provide said retraction force by tension in the spring member.

22. The device of claim 21 wherein a spring loaded arming bar is connected to the upper end portion of the elongated rod member, the spring loaded arming bar being engageable with a retainer member on the plunger and operable to exert a downward force sufficient to lock the needle assembly in operative position when the plunger is depressed, said arm being triggered by upward movement of the plunger to arm the spring member for retraction of the needle assembly.

23. The device of claim 22 wherein the arming bar is a continuation of the spring.

24. The device of claim 19 wherein said stop is positioned below the upper end of the elongated rod member to engage one end of the spring member and the opposite end of the spring member provides retraction force to the needle assembly by compression in the spring member.

25. The device of claim 24 wherein an arming bar is connected to the upper end portion of the elongated rod member, the arming bar being engageable with a retainer member on the plunger and operable to exert a downward force sufficient to lock the needle assembly in operative position when the plunger is depressed, said arming bar being triggered by upward movement of the plunger to arm the spring member for retraction of the needle assembly.

26. The device of claim 25 wherein the arming bar is a continuation of the spring.

* * * * *

UNITED STATES PATENT AND TRADEMARK OFFICE
CERTIFICATE OF CORRECTION

PATENT NO. : 5,188,613
DATED : February 23, 1993
INVENTOR(S) : Thomas J. Shaw

It is certified that error appears in the above-identified patent and that said Letters Patent is hereby corrected as shown below:

On the title page;

Under U.S. Patent Documents, add the following:

```
--4,747,831    5/1988     Kulli                604/110
  4,838,869    6/1989     Allard               604/195
  4,874,382   10/1989     Lindedmann, et al.   604/195
  4,904,242    2/1990     Kulli                604/110
  4,932,940    6/1990     Walker, et al.       604/110
  4,955,870    9/1990     Ridderheim, et al.   604/195
  5,007,903    4/1991     Ellard               604/195--
```

Signed and Sealed this

Fifth Day of November, 1996

Attest:

BRUCE LEHMAN

*Attesting Officer*      *Commissioner of Patents and Trademarks*